United States Patent [19]

Yoshinaga et al.

[11] Patent Number: 4,979,805
[45] Date of Patent: Dec. 25, 1990

[54] FERROELECTRIC LIQUID CRYSTAL DEVICE CONTAINING OPTICALLY ACTIVE AZO OR AZOXY BENZENE TYPE MESOMORPHIC COMPOUND WITH EXTENDED LIFE

[75] Inventors: Kazuo Yoshinaga, Tokyo; Kazuharu Katagiri, Tama, both of Japan

[73] Assignee: Canon Kabushiki Kaisha, Tokyo, Japan

[21] Appl. No.: 443,035

[22] Filed: Dec. 1, 1989

Related U.S. Application Data

[63] Continuation of Ser. No. 147,582, Jan. 21, 1988, abandoned, which is a continuation of Ser. No. 756,725, Jul. 19, 1985, abandoned.

[30] Foreign Application Priority Data

Jul. 23, 1984 [JP] Japan .................................. 59-151191
Jul. 23, 1984 [JP] Japan .................................. 59-151192

[51] Int. Cl.⁵ .................. C07C 283/08; C07C 245/06; G02F 1/135; C09K 19/24
[52] U.S. Cl. ........................... 350/350 R; 252/299.01; 252/299.1; 252/299.65; 252/299.68; 350/350 S; 534/566; 534/577; 534/649; 534/596; 560/35; 560/59; 560/61; 560/72; 560/73; 560/102; 560/106; 560/107; 560/108; 560/109
[58] Field of Search ................. 534/577, 566; 350/160 LC, 350 R, 350 S; 252/299.01, 299.1, 299.68

[56] References Cited

U.S. PATENT DOCUMENTS

| | | | |
|---|---|---|---|
| 3,815,972 | 6/1974 | Hsieh | 534/577 X |
| 3,816,334 | 6/1974 | Yamazaki | 534/577 X |
| 3,893,994 | 7/1975 | Steinstrader | 534/577 |
| 4,556,727 | 12/1985 | Walba | 534/577 X |
| 4,576,732 | 3/1986 | Isogai et al. | 534/577 X |
| 4,681,404 | 7/1987 | Okada | 350/350 S |

FOREIGN PATENT DOCUMENTS

| | | | |
|---|---|---|---|
| 2024269 | 12/1971 | Fed. Rep. of Germany | 534/577 |
| 2148178 | 3/1972 | Fed. Rep. of Germany | 534/577 |
| 2235397 | 4/1973 | Fed. Rep. of Germany | 534/577 |
| 51-1425 | 8/1976 | Japan | 534/577 |
| 51-1427 | 8/1976 | Japan | 534/577 |
| 1435269 | 5/1976 | United Kingdom | 534/577 |

*Primary Examiner*—Flyod D. Higel
*Attorney, Agent, or Firm*—Fitzpatrick, Cella, Harper & Scinto

[57] ABSTRACT

A ferroelectric liquid crystal composition containing an optically active mesomorphic compound represented by the following formula (I) or (II):

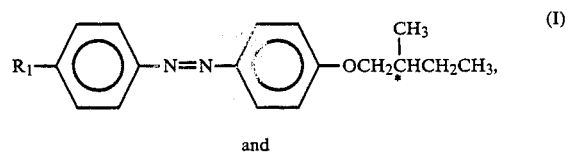

and

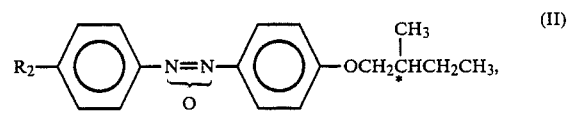

wherein $R_1$ and $R_2$ are respectively an alkyl, and C with * represents an asymmetric carbon atom. The mesomorphic compound provides the ferroelectric liquid crystal composition with an extended operational life in a liquid crystal device.

9 Claims, 1 Drawing Sheet

F I G. 1

F I G. 2

FERROELECTRIC LIQUID CRYSTAL DEVICE CONTAINING OPTICALLY ACTIVE AZO OR AZOXY BENZENE TYPE MESOMORPHIC COMPOUND WITH EXTENDED LIFE

This application is a continuation of application Ser. No. 147,582, filed Jan. 21, 1988, now abandoned, which is a continuation of application Ser. No. 756,725, filed July 19, 1985, now abandoned.

BACKGROUND OF THE INVENTION

The present invention relates to a novel mesomorphic compound, a liquid crystal composition containing the mesomorphic compound adapted for use in liquid optical devices such as display devices and optical shutters.

Chemical compounds having an optically active group have called attention for use as mesomorphic compounds. Chemical compounds characterized by optically active groups have been known to have such functions or usages as follows (i) guest-host electrooptical effect of the White-Taylor type utilizing a chiral nematic phase in a liquid crystal state; (ii) phase transition in an electric field from chiral nematic phase into nematic phase; (iii) phase transition between chiral nematic phase and smectic phase due to heat, (iv) ferroelectricity of smectic phase; (v) a non-linear optical element when formed into a film formed by accumulation of single molecules; and (vi) circular polarization beam-splitter or filter when fixed in a matrix. Therefore, extensive research has been made in order to find chemical compounds adapted for various usages as mentioned above by synthesizing various compounds having chemically active groups and examining their functions.

On the other hand, in the field of liquid crystal devices, there has been a well known type of liquid crystal devices using TN (twisted nematic) type liquid crystals as shown, for example, in "Voltage-Dependent Optical Activity of a Twisted Nematic Liquid Crystal" by M. Schadt and W. Helfrich, Applied Physics Letters Vol. 18, No. 4 (Feb. 15, 1971) pp. 127-128. In this type of liquid crystal devices, the number of picture elements have been restricted, because there is a problem that a crosstalk phenomenon occurs when a device of a matrix electrode structure with a high density of picture elements is driven according to a time-sharing or time-division driving scheme.

As another type of liquid crystal device, there has been known one comprising a plurality of picture elements each connected to and subject to switching by a thin film transistor as a switching element. This type of liquid crystal device, however, is accompanied with problems such that production of thin film transistors on a substrate is very complicated, and production of a display device with a large picture area or screen is difficult.

In order to obviate the above-mentioned drawbacks of the conventional types of liquid crystal devices, Clark and Lagerwall have proposed the use of a liquid crystal device using a bistable liquid crystal (Japanese Laid-Open Patent Application No. 107216/1981, U.S. Pat. No. 4367924, etc.). The bistable liquid crystal to be used may be a ferroelectric liquid crystal having a chiral smectic C (SmC*) phase, chiral smectic H (SmH*) phase, chiral smectic F (SmF*) phase, chiral smectic I (SmI*) phase or chiral smectic G (SmG*) phase.

Such a ferroelectric liquid crystal has bistability, i.e., has two stable states comprising a first stable state and a second stable state. Accordingly, different from the conventional TN-type liquid crystal in the above-mentioned device, the liquid crystal is oriented to the first stable state in response to one electric field vector and to the second stable state in response to the other electric field vector. Further, this type of liquid crystal very quickly assumes either one of the above-mentioned two stable states in reply to an electric field applied thereto and retains the state in the absence of an electric field. By utilizing these properties, essential improvements can be attained with respect to the above-mentioned difficulties involved in the conventional TN-type liquid crystal device.

For such bistable ferroelectric liquid crystal devices, there have hitherto been used such compounds as p-decyloxybenzylidene-p'-amino-2-methylbutyl cinnamate (DOBAMBC), p-hexyloxybenzylidene-p'-amino-2-chloropropyl cinnamate (HOBACPC) and 4-o-(2-methyl)-butylresorcylidene-4'-octylaniline (MBRA 8). However, these compounds are liable to be degraded when repeatedly subjected to application of electric field and therefore require that great care should be excercised in respect of tightness of sealing of cells, sealing conditions and driving conditions, thus providing a serious obstacle to development of the liquid crystal device. On the other hand, research has been made to find stable liquid crystal or mesomorphic compounds, whereas no practical compounds satisfying high response speed and stability have been found.

SUMMARY OF THE INVENTION

A principal object of the present invention is to provide a significant step to the solution of the above described problems.

More specifically, the present invention provides a mesomorphic compound represent by the following formula (I) or (II):

and wherein $R_1$ and $R_2$ are respectively an alkyl, and C with * represents an asymmetric carbon atom.

The present invention also provides a liquid crystal composition containing, as a constituent, the above-mentioned mesomorphic compound.

These and other objects, features and advantages of the present invention will become more apparent upon a consideration of the following description of the preferred embodiments of the present invention taken in conjunction with the accompanying drawings.

DETAILED DESCRIPTION OF THE PREFERRED EMBODIMENTS

The mesomorphic compound of the invention is expressed by the above formula (I) or (II).

If the alkyl group $R_1$ has too short a chain length in the formula (I), the compound has a defect that it lacks stability and provides a high phase transition temperature when it is mixed with a ferroelectric liquid crystal. On the other hand, too long a chain length results in increase in melting point and increase in viscosity. For an appropriate balance between the above properties, the alkyl group $R_1$ should preferably have a number of carbon atoms in the range of 4 to 20, more preferably 6 to 16, particularly preferably 6 to 12.

Preferred examples of 4-($\beta$-methylbutyloxy)-4'-alkylazobenzenes represented by the above-mentioned formula (I) include S-(+)-4-($\beta$-methylbutyloxy)-4'-butylazobenzene, S-(+)-4-($\beta$-methylbutyloxy)-4'-heptylazobenzene, S-(+)-4-($\beta$-methylbutyloxy)-4'-hexylazobenzene, S-(+)-4-($\beta$-methylbutyloxy)-4'-heptylazobenzene, S-(+)-4-($\beta$-methylbutyloxy)-4'-octylazobenzene, S-(+)-4-($\beta$-methylbutyloxy)-4'-nonylazobenzene, S-(+)-4-(8-methylbutyloxy)-4'-decylazobenzene, S-(+)-4-(8-methylbutyloxy)-4'-undecylazobenzene, and S-(+)-4-(8-methylbutyloxy)-4'-dodecylazobenzene.

The mesomorphic compound of the formula (I) as described above may, for example, be produced in the following manner.

To a p-alkylaniline under cooling is added an aqueous hydrochloric acid solution to form a hydrochloric acid salt. Then, an aqueous sodium nitride solution is added thereto to form a diazonium salt. An aqueous solution of the diazonium salt is added dropwise to phenol under alkaline condition to produce 4'-alkyl-4-hydroxyazobenzene. The 4'-alkyl-4-hydroxyazobenzene is, after purification, reacted with an excess of potassium hydroxide to produce an objective compound.

The above series of reactions are expressed by the following scheme:

Similarly as the mesomorphic compound of the formula (I), the compound of the formula (II) as another embodiment of the mesomorphic compound according to the present invention, if the alkyl group $R_2$ therein is too short, has a defect that it lacks stability and provides a high phase transition temperature when it is mixed with a ferroelectric liquid crystal. On the other hand, too long a chain length results in increase in melting point and increase in viscosity. From an appropriate balance between the above properties, the alkyl group $R_2$ should preferably have a number of carbon atoms in the range of 4 to 20, more preferably 6 to 16, particularly preferably 6 to 12.

Preferred examples of 4-($\beta$-methylbutyloxy)-4'-alkylazoxybenzenes represented by the above mentioned formula (II) include S-(+)-4-($\beta$-methylbutyloxy)-4'-butylazoxybenzene, S-(+)-4-($\beta$-methylbutyloxy)-4'-heptylazoxybenzene, S-(+)-4-($\beta$-methylbutyloxy)-4'-hexylazoxybenzene, S-(+)-4-($\beta$-methylbutyloxy)-4'-heptylazoxybenzene, S-(+)-4-($\beta$-methylbutyloxy)-4'-octylazoxybenzene, S-(+)-4-($\beta$-methylbutyloxy)-4'-nonylazoxybenzene, S-(+)-4-($\beta$-methylbutyloxy)-4'-decyloazoxybenzene, S-(+)-4-($\beta$-methylbutyloxy)-4'-undecylazoxybenzene, and S-(+)-4-($\beta$-methylbutyloxy)-4'-dodecylazoxybenzene.

The mesomorphic compound of the formula (II) as described above may be produced in the following manner.

To a p-alkylaniline under cooling is added an aqueous hydrochloric acid solution to form a hydrochloric acid salt. Then, an aqueous sodium nitrite solution is added thereto to form a diazonium salt. An aqueous solution of the diazonium salt is added dropwise to phenol under alkaline condition to produce 4'-alkyl-4-hydroxyazobenzene. The 4'-alkyl-4-hydroxyazobenzene is, after purification, reacted with excess potassium hydroxide and with 2'-methylbutyl bromide to produce 4-($\beta$-methylbutyloxy)-4'-alkylazobenzene. The compound is, after purification, dissolved in glacial acetic acid and heated to 60° to 70° C., and an aqueous hydrogen peroxide solution is added thereto to cause a reaction. The product is separated and purified to obtain- 4-(8-methylbutyloxy)-4'-alkylazoxybenzene.

The above series of reactions are expressed by the following scheme:

The mesomorphic compound of the formula (I) or (II) thus obtained is an optically active compound and mainly shows a cholesteric phase. When this compound is added in a small amount to a nematic liquid crystal, a liquid crystal composition is obtained, which is used for a White-Taylor type display device or a display device utilizing a phase transition from a chiral nematic phase to a nematic phase. Further, when this compound is added to a liquid crystal composition for a TN type display device, occurrence of reverse domain can be prevented.

Examples of the liquid crystal compounds to be used in connection with the mesomorphic compound of the general formula (I) or (II) for giving a ferroelectric liquid crystal composition according to the present invention include liquid crystal compounds showing a chiral smectic phase, preferably ferroelectric liquid crystal compounds showing a chiral smectic C or H phase.

Specific examples of the ferroelectric liquid crystal for use in the liquid crystal composition according to the present invention will be enumerated hereinbelow:

Schiff base-type ferroelectric liquid crystal compound:
(1) DOBAMBC (p-decyloxybenzylidene-p'-amino-2-methylbutyl cinnamate)

(The compounds obtained by replacing the p-decyloxy group with p-hexyloxy, p-heptyloxy, p-octyloxy or p-nonyloxy group also show ferroelectricity and may be used in the composition of the present invention.)

(2) DOBAMBCC (p-decyloxybenzylidene-p-amino-2-methylbutyl α-cyanocinnamate)

(The compound obtained by replacing the p-decyloxy group with p-tetradecyloxy group also shows ferroelectricity.)

(3) OOBAMBCC (p-octyloxybenzylidene-p'-amino-2-methylbutyl α-chlorocinnamate)

(4) HOBACPC (p-hexyloxybenzylidene-p'-amino-2-chloropropyl cinnamate)

(The compounds having an alkoxy group ranging from p-hexyloxy to p-dodecyloxy in this series show ferroelectricity.)

(5) OOBAMBMC (p-octyloxybenzylidene-p'-amino-2-methylbutyl α-methylcinnamate)

(6) DOBMBA (p-decyloxybenzylidene-p-(2-methyloxycarbonyl)aniline)

(The compounds having an alkoxy group ranging from p-heptyloxy to p-tetradecyloxy in this series show ferroelectricity.)

Ester-type ferroelectric liquid crystal compounds:
(1) 4-n-hexyloxyphenyl 4-(2'-methylbutyl)biphenyl-4'-carboxylate

(2) 4-(2'-methylbutyl)phenyl 4'-octylbiphenyl-4-carboxylate (3) 2-(2'-methylbutyloxy)phenyl 4'-dodecyloxyphenyl-4-carboxylate (The compound obtained by replacing the 2'-methylbutyloxy group with 4'-nonyloxy group also shows ferroelectricity.)

Azoxy-type ferroelectric liquid crystal compound:
(1) PACMB (p-azoxycinnamate 2-methylbutanol)

The liquid crystal composition of the present invention may comprise two or more species, respectively, from the ferroelectric liquid crystal compounds and from the compounds expressed by the general formula (I) or (II).

The composition according to the present invention comprises 4-(β-methylbutyloxy)-4'-alkylazobenzene expressed by the general formula (I) or 4-(β-methylbutyloxy)-4'-alkylazoxybenzene expressed by the general formula (II) in an amount of 0.01 to 100 parts by weight with respect to 100 parts by weight of a ferroelectric liquid crystal compound. If the amount is less than 0.01 part by weight, an effect of extending the operation life cannot be attained. When the amount exceeds 100 parts by weight, the ferroelectric liquid crystal compound is diluted in the composition and the ferroelectric electric characteristic of the composition is impaired.

Figure 1:
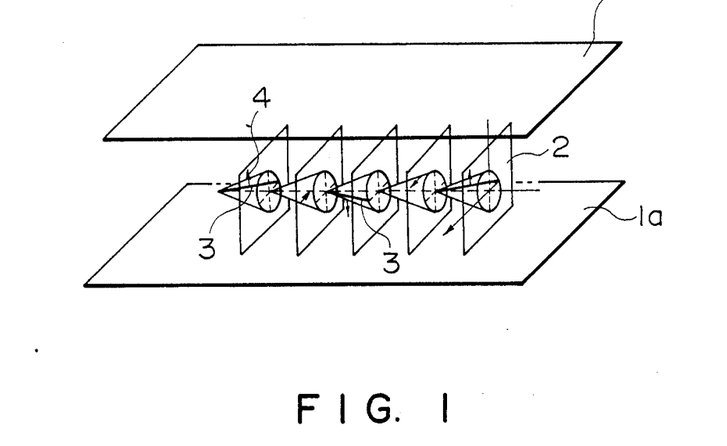
FIGS. 1 and 2 are schematic perspective views illustrating the basic operation principle of a liquid crystal cell used in the present invention.
Figure 2:
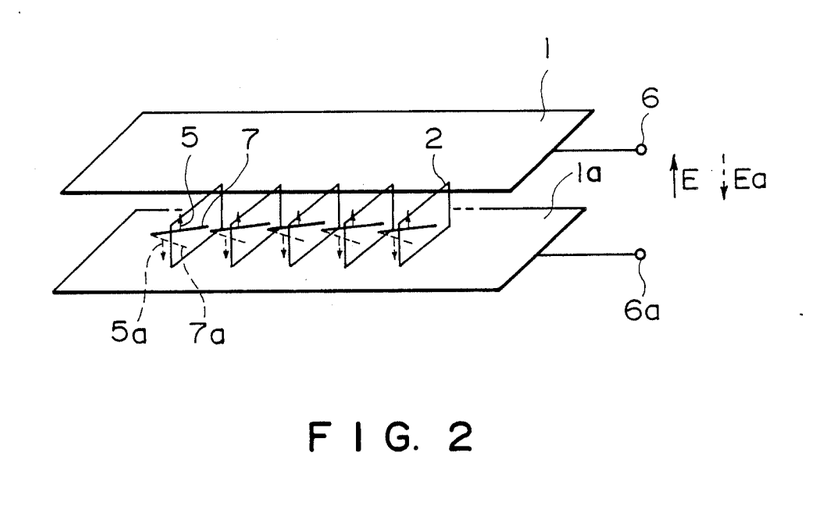

Next, the operation principle of a ferroelectric liquid crystal is explained with reference to FIGS. 1 and 2. FIG. 1, reference numerals 1 and 1a denote base plates (glass plates) on which a transparent electrode of, e.g., $In_2O_3$, $SnO_2$, ITO (Indium-Tin Oxide), etc., is disposed respectively. A liquid crystal of a chiral smectic phase such as SmC* phase, SmH* phase, etc., in which liquid crystal molecular layers 2 are oriented perpendicular to surfaces of the glass plates is hermetically disposed therebetween. A full line 3 shows liquid crystal molecules. Each liquid crystal molecule 3 has a dipole moment (P⊥) 4 in a direction perpendicular to the axis thereof. When a voltage higher than a certain threshold level is applied between electrodes formed on the base plates 1 and 1a, a helical structure of the liquid crystal molecule 3 is loosened or unwound to change the alignment direction of respective liquid crystal molecules 3 so that the dipole moments (P⊥) 4 are all directed in the direction of the electric field. The liquid crystal molecules 3 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage. The liquid crystal layer in the liquid crystal device of the present invention may preferably be rendered sufficiently thin in thickness (e.g., less than 10 μ). As the thickness of the liquid crystal layer is decreased, the helical structure of the liquid crystal molecules is loosened even in the absence of an electric field whereby the dipole moment assumes either of the two states, i.e., P in an upper direction 5 or Pa in a lower direction 5a as shown in FIG. 2. When electric field E or Ea higher than a certain threshold level and different from each other in polarity as shown in FIG. 2 is applied to a cell having the above-mentioned characteristics by means of voltage application means 6 and 6a, the dipole moment is directed either in the upper direction 5 or in the lower direction 5a depending on the vector of the electric field E or Ea. In correspondence with this, the liquid crystal molecules are oriented in either of a first stable state 7 or a second stable state 7a.

When the above-mentioned ferroelectric liquid crystal is used as an optical modulation element, it is possible to obtain two advantages as briefly discussed hereinbefore. First is that the response speed is quite fast. Second is that the orientation of the liquid crystal shows bistability. The second advantage will be further explained, e.g., with reference to FIG. 2. When the electric field E is applied to the liquid crystal molecules, they are oriented in the first stable state 7. This state is kept stable even if the electric field is removed. On the other hand, when the electric field 7a of which direction is opposite to that of the electric field E is applied thereto, the liquid crystal molecules are oriented to the second stable state 7a, whereby the directions of molecules are changed. This state is similarly kept stable even if the electric field is removed. Further, as long as the magnitude of the electric field E being applied is not -above a certain threshold value, the liquid crystal molecules are placed in the respective orientation states. In order to effectively realize high response speed and bistability, it is preferable that the thickness of the cell be as thin as possible.

[EXAMPLES]

The present invention will be explained by way of specific examples.

In the following examples, the phase transition temperature was measured by a DSC (differential scanning calorimeter) (SSC 580 DS, manufactured by Seiko Denshi K.K.), and the phase transition was confirmed by placing a liquid crystal sealed between glass plates in a copper block under temperature control and observing it through a polarizing microscope.

EXAMPLE 1

Production of
S-(+)-4-(β-methylbutyloxy)-4'-heptylazobenzene 32.9 g (0.17M) of 4-heptylaniline was cooled below 0° C. and 85 g of 10% aqueous hydrochloric acid solution was added thereto. To the mixture was then added dropwise an aqueous solution of 12.1 g of sodium nitrite in 70 ml of water while cooling the mixture so as not to exceed 0° C. After the dropwise addition, the reaction was continued for 30 minutes. The reaction mixture was transferred into a dropping funnel and added dropwise therefrom into 300 ml of an 8%-NaOH aqueous solution containing 16 g of phenol while the temperature was kept below 5° C. After the dropwise addition, stirring was continued for 1 hour, and thereafter a 10% aqueous hydrochloric acid solution was added until the pH reached 5 to 6 thereby precipitating the reaction product. The precipitate was placed on a filter, washed with water and dried under reduced pressure overnight. The dried product was washed with 500 ml of petroleum ether and dried under reduced pressure to obtain 34.7 g (0.12M) of 4-hydroxy-4'-heptylazobenzene. The yield was 70%.

10 g (0.034M) of the 4-hydroxy-4'-heptylazobenzene was dissolved in 20 ml of ethanol together with 4.4 g of potassium hydroxide and heated under reflux for 6 hours. Then, 10 g of S-(+)-2-methylbutyl bromide was added thereto and the mixture was heated under reflux for 12 hours. After the completion of the reaction, the reaction product was filtered and the solvent was distilled off therefrom. The residue was dissolved in benzene and subjected to column chromatography with silica gel. After the benzene was distilled off, the residue was dried under reduced pressure to obtain 5.0 g (0.014M) of S-(+)-4-(β-methylbutyloxy)-4'-heptylazobenzene. The yield was 41%.

The IR (infrared absorption) and NMR (nuclear magnetic resonance) data and phase transition temperatures of the compound are shown as follows:

IR: —N=N— 1600 cm⁻¹; Ar—O—CH₂ 1240 cm⁻¹

NMR(δppm);

| Ar—C$\underline{H_2}$— | 2.6(t) |
| 0.8–2.0 | methyl, methylene |
| A—O—C$\underline{H_2}$— | 3.7(q) |
| A$\underline{r}$ | 6.7–7.9 |

Phase transition temperature:

The abbreviations used herein and in the examples appearing hereinafter represent the following:
Cryst: crystal,
Ch: cholesteric phase,
Iso: isotropic liquid.

EXAMPLE 2

Production of
S-(+)-4-(β-methylbutyloxy)-4'-hexylazobenzene 30.1 g (0.17M) of 4-hexylaniline was cooled below 0° C. and 85 g of 10% aqueous hydrochloric acid solution was added thereto. To the mixture was then added dropwise an aqueous solution of 11.6 g of sodium nitrite in 68 g of water while cooling the mixture so as not to exceed 0° C. After the dropwise addition, the reaction was continued for 30 minutes. The reaction mixture was transferred into a dropping funnel and added dropwise therefrom into 170 g of an 8%-NaOH aqueous solution containing 16 g of phenol while the temperature was kept below 5° C. After the dropwise addition, stirring was continued for 0.5 hour, and thereafter a 10% aqueous hydrochloric acid solution was added until the pH reached 5–6 thereby precipitating the reaction product. The precipitate was separated by filtration, washed with water and dried under reduced pressure overnight. The dried product was washed with 500 ml of petroleum ether and dried under reduced pressure to obtain 29.6 g (0.10M) of 4-hydroxy-4'-hexylazobenzene The yield was 59%.

8.6 g (0.030M) of the 4-hydroxy-4'-hexylazobenzene was dissolved in 20 ml of ethanol together with 3.3 g of potassium hydroxide and heated under reflux for 9 hours. Then, 9.0 g of S-(+)-2-methylbutyl bromide was added thereto and the mixture was heated under reflux for 12 hours. After the completion of the reaction, the reaction product was filtered and the solvent was distilled off therefrom. The residue was dissolved in benzene and subjected to column chromatography with silica gel. After the benzene was distilled off, the residue was dried under reduced pressure to obtain 5.9 g (0.017M) of S-(+)-4-(β-methylbutyloxy)-4'-hexylazobenzene. The yield was 57%.

The IR and NMR data and phase transition temperatures of the compound are shown as follows:

IR: —N=N— 1605 cm⁻¹; Ar—O—CH₂ 1250 cm⁻¹

NMR(δppm);

| Ar—C$\underline{H_2}$— | 2.7(t) |
| 0.8–2.0 | methyl, methylene |
| Ar—O—C$\underline{H_2}$— | 3.9(q) |
| A$\underline{r}$ | 7–8 |

Phase transition temperature:

EXAMPLE 3

Production of
S-(+)-4-(β-methylbutyloxy)-4'-octylazobenzene 35 g (0.17M) of 4-octylaniline was cooled below 0° C. and 85 g of 10% aqueous hydrochloric acid solution was added thereto. To the mixture was then added dropwise an aqueous solution of 12.0 g of sodium nitrite in 68 ml of water while cooling the mixture so as not to exceed 0° C. After the dropwise addition, the reaction was continued for 30 minutes. The reaction mixture was transferred into a dropping funnel and added dropwise therefrom into 170 g of an 8%-NaOH aqueous solution containing 16 g of phenol while the temperature was kept below 5° C. After the dropwise addition, stirring was continued for 1 hour, and thereafter a 10% aqueous hydrochloric acid solution was added until the pH reached 5–6 thereby precipitating the reaction product. The precipitate was separated by filtration, washed with water and dried under reduced pressure overnight. The dried product was washed with 500 ml of petroleum ether and dried under reduced pressure to obtain 30.8 g (0.10M) of 4-hydroxy-4'-octylazobenzene. The yield was 59%.

10 g (0.032M) of the 4-hydroxy-4'-octylazobenzene was dissolved in 20 ml of ethanol together with 3.6 g of potassium hydroxide and heated under reflux for 6 hours. Then, 9 g of S-(+)-2-methylbutyl bromide was added thereto and the mixture was heated under reflux for 12 hours. After the completion of the reaction, the reaction product was filtered and the solvent was distilled off therefrom. The residue was dissolved in benzene and subjected to column chromatography with silica.gel. After the benzene was distilled off, the residue was dried under reduced pressure to obtain 5.7 g (0.015M) of S-(+)-4-(β-methylbutyloxy)-4'-octylazobenzene. The yield was 47%.

The IR and NMR data and phase transition temperatures of the compound are shown as follows:
IR: —N=N— 1610 cm$^{-1}$; Ar—O—CH$_2$ 1255 cm$^{-1}$
NMR(δppm):

| | |
|---|---|
| Ar—CH$_2$— | 2.5(t) |
| 0.8–2.0 methyl, methylene | |
| Ar—O—CH$_2$— | 3.7(q) |
| Ar | 6.8–7.9 |

Phase transition temperature:

EXAMPLE 4

Production of S-(+)-4-(β-methylbutyloxy)-4'-heptylazoxybenzene 2.0 g (0.0055M) of the S-(+)-4-(β-methylbutyloxy)-4'-heptylazobenzene prepared in Example 1 was dissolved in 50 ml of glacial acetic acid and the mixture was stirred under heating at 60°–70° C. To the mixture was added 1 ml of 30% aqueous solution of hydrogen peroxide and a reaction proceeded for 4 hours. Thereafter, 4 ml of 30%-hydrogen peroxide aqueous solution was added dropwise in 8 hours and a reaction proceeded for 6 hours after the completion of the dropwise addition. After the completion of the reaction, the reaction product was extracted with hexane and the solvent was distilled off. The product was dissolved in benzene and subjected to column chromatography with silica gel. The benzene was distilled off and the residue was dried under reduced pressure to obtain 1.8 g (0.0047 M) of S-(+)-4-(β-methylbutyloxy)-4'-heptylazoxybenzene). The yield was 85%.

The IR and NMR data as well as the phase transition temperatures of the compound are as follows.
IR:

| | |
|---|---|
| —N=N—<br>∥<br>O | 1605 cm$^{-1}$, 1280 cm$^{-1}$ |
| Ar—O—CH$_2$ | 1260 cm$^{-1}$ |

NMR:

| | |
|---|---|
| Ar—CH$_2$— | 2.5(t) |
| 0.7–2.0 methyl, methylene | |
| Ar—O—CH$_2$— | 3.7(q) |
| Ar | 7.7–8.2 |

Phase transition temperature:

EXAMPLE 5

Production of S-(+)-4-(β-methylbutyloxy)-4'-hexylazoxybenzene 2.5 g (7.1×10$^{-3}$M) of the S-(+)-4-(β-methylbutyloxy)-4'-hexylazobenzene prepared in Example 2 was dissolved in 50 ml of glacial acetic acid and the mixture was stirred under heating at 60°–70° C. To the mixture was added 1 ml of 30% aqueous solution of hydrogen peroxide and a reaction proceeded for 4 hours. Thereafter, 4 ml of 30% hydrogen peroxide aqueous solution was added dropwise in 8 hours and a reaction proceeded for 6 hours after the completion of the dropwise addition. After the completion of the reaction, the reaction product was extracted with hexane and the solvent was distilled off. The product was dissolved in benzene and subjected to column chromatography with silica gel. The benzene was distilled off and the residue was dried under reduced pressure to obtain 1.7 g (4.6×10$^{-3}$M) of S-(+)-4-(β-methylbutyloxy)-4'-hexylazoxybenzene). The yield was 65%.

The IR and NMR data as well as the phase transition temperatures of the compound are as follows.
IR:

| | | |
|---|---|---|
| —N=N—<br>∥<br>O | 1595 cm$^{-1}$, | 1270 cm$^{-1}$ |
| Ar—O—CH$_2$ | 1245 cm$^{-1}$ | |

NMR(δppm):

| | |
|---|---|
| Ar—CH$_2$— | 2.6(t) |
| 0.7–2.0 methyl, methylene | |
| Ar—O—CH$_2$— | 3.7 |
| Ar | 6.7–8.3 |

Phase transition temperature:

EXAMPLE 6

Production of S-(+)-4-(β-methylbutyloxy)-4'-octylazoxybenzene 2.1 g (5.5×10$^{-3}$M) of the S-(+)-4-(β-methylbutyloxy)-4'-octylazobenzene prepared in Example 3 was dissolved in 50 ml of glacial acetic acid and the mixture was stirred under heating at 60°–70° C. To the mixture added 1 ml of 30% aqueous solution of hydrogen peroxide and a reaction was proceeded for 4 hours. Thereafter, 4 ml of 30% hydrogen peroxide aqueous solution added dropwise in 8 hours and a reaction was proceeded for 6 hours after the completion of the dropwise addition. After the completion of the reaction, the reaction product was extracted with hexane and the solvent was distilled off. The product was dissolved in benzene and subjected to column chromatography with silica gel. The benzene was distilled off and the residue was dried under reduced pressure to obtain 1.7 g (4.3×10⁻³M) of S-(+)-4-(β-methylbutyloxy)-4'-octylazoxybenzene). The yield was 78%.

The IR data and the phase transition temperatures of the compound are as follows.

IR:

Phase transition temperature:

EXAMPLE 7

A liquid crystal composition was prepared by adding 6 parts by weight of S-(+)-4-(β-methylbutyloxy)-4'-heptylazobenzene to 100 parts by weight of DO-BAMBC.

Separately, on a square glass base plate were formed ITO electrode film in the form of stripes with a width of 62.5 μm at a pitch of 100 μm. In an apparatus for the oblique vapor deposition, the base plate was disposed with its face having the ITO film being directed downward and a crystal of SiO₂ was set in a crucible of molybdenum. Then the vapor deposition apparatus was evacuated to a vacuum of the order of 10⁻⁵ Torr and SiO₂ was obliquely vapor-deposited in a prescribed manner to form an electrode plate with an 800 Å-thick oblique vapor deposition film (A electrode plate).

On the other hand, on a similar glass plate provided with stripe-form ITO electrode films was applied a polyimide forming solution ("PIQ": polyimide-isoindolquinazoline-dione, produced by Hitachi Kasei Kogyo K.K.; Non-volatile content: 14.5 wt. %) by means of a spinner coater, which was then heated at 120° C. for 30 minutes, at 200° C. for 60 minutes and at 350° C. for 30 minutes to form a film of 800 Å in thickness (B electrode plate).

Then, a heat-setting epoxy adhesive was applied to the periphery of the A electrode plate except for the portion forming an injection port by screen printing process. The A electrode plate and the B electrode plate were superposed with each other so that their stripe-pattern electrodes crossed each other at right angles and were secured to each other with a polyimide spacer while leaving the gap of 2 μ therebetween, thereby to form a cell (blank cell).

The above mentioned liquid crystal composition was heated into the isotropic phase and injected through the injection port of the thus-prepared blank cell, and the injection port was sealed. The liquid crystal cell thus formed was gradually cooled and, at a constant temperature of about 65° C., was observed through a microscope while being sandwiched between a pair of polarizers arranged in the cross nicol relationship, whereby a monodomain of SmC* phase whose spiral had been loosened was found to be formed.

Then, to the liquid crystal cell at the same temperature was repeatedly applied a rectangular wave voltage of 40V (peak-to-peak) and 100 Hz. The deterioration of the liquid crystal cell was evaluated by comparing the initial current and the current after 500 hours of the continuous operation, whereby they were 0.6 μA at the initial stage and 0.7 μA after the continuous operation.

EXAMPLE 8

A liquid crystal cell was prepared in the same manner as in Example 7 except that the liquid crystal composition was replaced by one comprising 100 parts by weight of DOBAMBC, 4 parts by weight of S-(+)-4-(β-methylbutyloxy)-4'-octyloazobenzene and 4 parts by weight of S-(+)-4-(β-methylbutyloxy)-4'-decyloazobenzene.

The deterioration of the liquid crystal cell was evaluated similarly as in Example 7 by comparing the current values before and after the continuous operation, whereby the current value was 0.5 μA at the initial stage and 0.6 μA after the continuous operation.

COMPARATIVE EXAMPLE 1

A liquid crystal cell was prepared in the same manner as in Example 7 except that S-(+)-4-(β-methylbutyloxy)-4'-heptylazobenzene was omitted from the liquid crystal composition. The liquid crystal cell was evaluated in the same manner as in Example 7 by measuring electric currents, whereby the current was 0.6 μA at the initial stage and 1.1 μA after the continuous operation.

As is apparent from the above Examples and Comparative Example, the life of a liquid crystal device can be remarkably extended by adding a 4-(β-methylbutyloxy)-4'-alkylazobenzene to form a liquid crystal composition to be used.

EXAMPLE 9

A liquid crystal composition was prepared by adding 5 parts by weight of S-(+)-4-(β-methylbutyloxy)-4-heptylazoxybenzene to 100 parts by weight of DO-BAMBC.

Separately, on a square glass base plate were formed ITO electrode film in the form of stripes with a width of 62.5 μm at a pitch of 100 μm. In an apparatus for the oblique vapor deposition, the base plate was disposed with its face having the ITO film being directed downward and a crystal of SiO₂ was set in a crucible of molybdenum. Then the vapor deposition apparatus was evacuated to a vacuum of the order of 10⁻⁵ Torr and SiO₂ was obliquely vapor-deposited in a prescribed manner to form an electrode plate with an 800 Å-thick° oblique vapor deposition film (A electrode plate).

On the other hand, on a similar glass plate provided with stripe-form ITO electrode films was applied a polyimide-forming solution ("PIQ": polyimide-isoindolquinazoline-dione, produced by Hitachi Kasei Kogyo K.K.; Non-volatile content: 14.5 wt. %) by means of a spinner coater, which was then heated at 120° C. for 30 minutes, at 200° C. for 60 minutes and at 350° C. for 30 minutes to form a film of 800 ° A in thickness (B electrode plate).

Then, a heat-setting epoxy adhesive was applied to the periphery of the A electrode plate except for the portion forming an injection port by screen printing process. The A electrode plate and the B electrode plate were superposed with each other so that their stripe-pattern electrodes crossed each other at right angles and were secured to each other with a polyimide spacer while leaving the gap of 2 μ therebetween, thereby to form a cell (blank cell).

The above-mentioned liquid crystal composition was heated into the isotropic phase and injected through the injection port of the thus prepared blank cell, and the injection port was sealed. The liquid crystal cell thus formed was gradually cooled and, at a constant temperature of about 65° C., was observed through a microscope while being sandwiched between a pair of polarizers arranged in the cross nicol relationship, whereby a monodomain of SmC* phase whose spiral had been loosened was found to be formed.

Then, to the liquid crystal cell at the same temperature was repeatedly applied a rectangular wave voltage of 40V (peak-to-peak) and 100 Hz. The deterioration of the liquid crystal cell was evaluated by comparing the initial current and the current after 500 hours of continuous operation, whereby they were 0.5 μA at the initial stage and 0.7 μA after the continuous operation.

EXAMPLE 10

A liquid crystal cell was prepared in the same manner as in Example 9 except that the liquid crystal composition was replaced by one comprising 100 parts by weight of DOBAMBC, 3 parts by weight of S-(+)-4-(8-methylbutyloxy)-4'-decylazoxybenzene and 2 parts by weight of S-(+)-4-(β-methylbutyloxy)-4'-dodecylazoxybenzene.

The deterioration of the liquid crystal cell was evaluated similarly as in Example 9 by comparing the current values before and after continuous operation, whereby the current value was 0.6 μA at the initial stage and 0.7 μA after the continuous operation.

COMPARATIVE EXAMPLE 2

A liquid crystal cell was prepared in the same manner as in Example 9 except that S-(+)-4-(β-methylbutyloxy)-4'-octylazoxybenzene was omitted from the liquid crystal composition. The liquid crystal cell was evaluated in the same manner as in Example 9 by measuring electric currents, whereby the current was 0.6 μA at the initial stage and 1.1 μA after continuous operation.

As is apparent from the above Example and Comparative Example, the life of a liquid crystal device can be remarkably extended by adding a 4-(β-methylbutyloxy)-4'-alkylazoxybenzene to form a liquid crystal composition to be used.

The novel compound according to the present invention of 4-(β-methylbutyloxy)-4'-alkylazobenzene or 4-(β-methylbutyloxy)-4'-alkylazoxybenzene shows mesomorphism and, when mixed with a ferroelectric liquid crystal compound, provides the liquid crystal composition according to the present invention. The liquid crystal composition has an extended operation life without imparing the characteristics of the ferroelectric liquid crystal compound and contributes to extension in operation life of a liquid crystal device. Thus, the composition is suitable for use in liquid crystal devices, liquid crystal optical shutters and therefore has a considerable commercial significance.

What is claimed is:

1. A ferroelectric chiral smectic liquid crystal device comprising:
  a cell, and
  a ferroelectric chiral smectic liquid crystal composition comprising a ferroelectric smectic liquid crystal compound and a compound of formula (I)

or formula (II)

wherein $R_1$ and $R_2$ are independently linear alkyl groups containing 6 to 16 carbon atoms, and C with * is an asymmetric carbon atom, said compound of formula (I) or (II) being present in an amount of 0.01 to 100 parts by weight with respect to 100 parts by weight of said ferroelectric chiral smectic liquid crystal compound.

2. A ferroelectric chiral smectic liquid crystal composition comprising a ferroelectric chiral smectic liquid crystal compound and a compound of formula (I)

or formula (II)

wherein $R_1$ and $R_2$ are independently linear groups containing 6 to 16 carbon atoms, and C with * is an asymmetric carbon atom, said compound of formula (I) or (II) being present in an amount of 0.01 to 100 parts by weight with respect to 100 parts by weight of said ferroelectric chiral smectic liquid crystal compound.

3. A ferroelectric liquid crystal composition according to claim 2, wherein the ferroelectric liquid crystal is a chiral smetic liquid crystal compound.

4. A ferroelectric liquid crystal composition according to claim 2, wherein the compound of formula (I) or formula (II) is present in the amount of 0.1 to 100 parts per 100 parts by weight of the ferroelectric liquid crystal compound.

5. The liquid crystal composition according to claim 2, wherein the ferroelectric liquid crystal compound is a Schiff base-type liquid crystal compound.

6. The liquid crystal composition according to claim 2, wherein the ferroelectric liquid crystal compound is an ester-type liquid crystal compound.

7. The liquid crystal composition according to claim 2, wherein the ferroelectric liquid crystal compound is an azoxy-type liquid crystal compound.

8. The liquid crystal composition according to claim 2, wherein the $R_1$ in the formula (I) is alkyl having 6 to 12 carbon atoms.

9. The liquid crystal composition according to claim 2, wherein the $R_2$ in the formula (II) is alkyl having 6 to 12 carbon atoms.

* * * * *

UNITED STATES PATENT AND TRADEMARK OFFICE
CERTIFICATE OF CORRECTION

PATENT NO. : 4,979,805

DATED : December 25, 1990

INVENTOR(S) : KAZUO YOSHINAGA ET AL.

It is certified that error appears in the above-identified patent and that said Letters Patent is hereby corrected as shown below:

Title page:

AT [56] REFERENCES CITED

U.S. Patent Documents,
        "Steinstrader" should read --Steinstrasser--.

Primary Examiner, "Flyod D. Higel" should read --Floyd D. Higel--.

COLUMN 3

Line 23, "(8-methylbutyloxy)" should read --($\beta$-methylbutyloxy)--.
    Line 24, "(8-methylbutyloxy)" should read --($\beta$-methylbutyloxy)--.
    Line 25, "(8-methylbutyloxy)" should read --($\beta$-methylbutyloxy)--.

COLUMN 4

Line 39, "(8-methyl-" should read --($\beta$-methyl---.

COLUMN 6

Line 21, "p-(2-methylox-" should read --p'-(2-methylox---.
    Line 32, "(2'-methylbutyl)" should read --(2"-methylbutyl)--.

COLUMN 9

Line 30, insert --NMR($\delta$ppm):--.

UNITED STATES PATENT AND TRADEMARK OFFICE
CERTIFICATE OF CORRECTION

PATENT NO. : 4,979,805
DATED : December 25, 1990
INVENTOR(S) : KAZUO YOSHINAGA ET AL.

It is certified that error appears in the above-identified patent and that said Letters Patent is hereby corrected as shown below:

COLUMN 15

Line 22, "S-(+)-4-(8-" should read --S-(+)-4-(β---.

COLUMN 15

Line 67, "smectic" should read --chiral smectic--.

COLUMN 16

Line 35, "  " should read

--  --.

Line 47, "smetic" should read --smectic--.

Signed and Sealed this

Twenty-ninth Day of September, 1992

Attest:

DOUGLAS B. COMER

Attesting Officer    Acting Commissioner of Patents and Trademarks